United States Patent [19]
Akhavan-Tafti

[11] Patent Number: 6,068,979
[45] Date of Patent: May 30, 2000

[54] SIMPLIFIED SEQUENTIAL CHEMILUMINESCENT DETECTION

[75] Inventor: Hashem Akhavan-Tafti, Brighton, Mich.

[73] Assignee: Lumigen, Inc., Southfield, Mich.

[21] Appl. No.: 09/064,451

[22] Filed: Apr. 22, 1998

[51] Int. Cl.[7] ............................ C12Q 1/68; G01N 33/53; G01N 33/535; G01N 33/545; G01N 33/552
[52] U.S. Cl. ................................ 435/6; 435/7.8; 435/7.9; 435/7.95; 435/973
[58] Field of Search ............................... 435/6, 7.94, 7.95, 435/7.8, 7.9, 973

[56] References Cited

U.S. PATENT DOCUMENTS

| | | |
|---|---|---|
| 4,931,223 | 6/1990 | Bronstein . |
| 5,656,207 | 8/1997 | Woodhead . |
| 5,672,475 | 9/1997 | Lee . |
| 5,744,320 | 4/1998 | Sherf . |

FOREIGN PATENT DOCUMENTS

| | | |
|---|---|---|
| WO97/24460 | 7/1997 | WIPO . |

OTHER PUBLICATIONS

S. Girotti et al, Analytical Biochemistry, vol. 236, 290–295, 1996.
S.Krajewski, J.M. Zapata, J.C. Reed, Anal. Biochem., 236, 221–228 (1996).
L. Au, K. Chang, C. Shih, G. Teh, BioTech. 16(4) 680–683 (1994).

*Primary Examiner*—Mary E. Ceperley
*Attorney, Agent, or Firm*—Richard S. Handley

[57] ABSTRACT

A method for sequential chemiluminescent detection of two differently labeled analytes on a single blot is described. In the method, a uniquely labeled DNA is detected with a horseradish peroxidase (HRP) substrate followed by the detection of another uniquely labeled DNA with a second different enzyme substrate which also inhibits the chemiluminescence generated by HRP. The sequential detection method described herein eliminates the need to strip and reprobe Southern, Northern and Western blots. Potential applications of this method include forensic DNA fingerprinting where more than one probe is used for probing a Southern blot, multiplex DNA sequencing of more than one template, detection of gene rearrangements, mutations and gene linkage.

30 Claims, 4 Drawing Sheets

1 2 3

A + B
SUPERIMPOSED

N/N  N/Δ  Δ/Δ

- B — BIOTIN
- D — DIGOXIGENIN
- X — AVIDIN

HRP DETECTION

N/N  N/Δ  Δ/Δ

AP DETECTION

N/N  N/Δ  Δ/Δ

A

B

|   |   |
  N/N | Δ/Δ
  N/Δ
  1  2  3

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:1:

ACTTCACTTC TAATGATGAT TATG                                    24

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:2:

CTCTTCTAGT TGGCATGCTT TGAT                                    24

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(xi) SEQUENCE DESCRIPTION: SEQ ID NO:3:

ATATCATCTT TGGTGTTTCC T                                       21

(2) INFORMATION FOR SEQ ID NO:4:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(xi) SEQUENCE DESCRIPTION: SEQ ID NO:4:

GAAAATATCA TTGGTGTTTC C                                       21

SIMPLIFIED SEQUENTIAL CHEMILUMINESCENT DETECTION

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. 2R44 DK47727-02 and 1R43 CA75830-01. Awarded by the National Institute of Health.

FIELD OF THE INVENTION

The present invention relates to a method for the sequential chemiluminescent detection of two analytes in a test system. In particular, the invention relates to methods in which the analytes are labeled with two different enzymes, more particularly when one of the enzymes is a peroxidase. The methods are preferably performed for the analysis of analytes on a solid phase such as a blotting membrane. The invention provides methods for the detection of multiple analytes on a solid phase which eliminates the need to strip and reprobe blots. The methods of the present invention are suitable for the detection of multiple DNA markers or probes on a single Southern blot, for forensic DNA fingerprinting where more than multiple probes are used, multiplex DNA sequencing of more than one template, detection of gene rearrangements, mutations and gene linkage, multiple proteins in Western blots and other assays known in the art.

BACKGROUND OF THE INVENTION

Numerous methods for the chemiluminescent detection of analytes such as DNA, RNA, proteins, antibodies, antigens, haptens, drugs, hormones, infectious agents and the like are known. Chemiluminescent detection can be performed by labeling analytes or molecules which specifically bind an analyte with a compound which can be made to undergo a chemiluminescent reaction (direct labeling). Chemiluminescent detection can be performed by labeling analytes or analyte-binding compounds with an enzyme or similar catalyst which catalyzes the chemiluminescent reaction of an added compound (enzyme labeling). The popularity of these modes of detection arises, in part, from the levels of sensitivity and wide range of measurement which is possible. Other favorable properties include safety, since no radioisotopes are required, versatility in the methods of labeling and choice of detection devices. In addition, in a commonly used format, probes are labeled with different haptens such as biotin, fluorescein and digoxigenin. These haptens, in turn, are then bound with their corresponding ligands or antibodies conjugated with an enzyme such as horseradish peroxidase (HRP) or alkaline phosphatase (AP). The label enzymes are detected with their respective chemiluminescent substrates.

It is frequently desirable to be able to detect and/or quantify more than one analyte at a time in a single test system. Savings in time, reagents and materials can thereby be realized and assay protocols can be simplified. In some instances information from multiple tests is required, for example, in certain medical diagnostic procedures, the results of two or more tests must be analyzed in combination in order to reach any conclusion. An exemplary technique requiring testing for multiple analytes is genetic fingerprinting of DNA samples for forensic, human identification or paternity determination tests by restriction fragment length polymorphism (RFLP) analysis of Southern blotted DNA. In this technique, blots require probing with several probes and often the limited amount of DNA necessitates the stripping and reprobing of the same blot multiple times (Adams, D. E., (1988), Crime Lab Digest 15:106–108; Noppinger, K., G. Duncan, D. Ferraro, S. Watson and J. Ban, (1992), BioTechniques. 13:572–575.). In Northern blot analysis, the expression of a specific gene is measured at the messenger RNA (mRNA) level and the signal is normalized by reprobing the blot for mRNAs such as α-tubulin or β-actin that are normally invariant in the cell. In a Western blot of multiple protein antigens, the antibodies hybridized in one step are stripped and reprobed with another set of antibodies in an additional step to obtain data for another protein.

Stripping and reprobing may result in the loss of membrane bound target nucleic acids (Noppinger, K., G. Duncan, D. Ferraro, S. Watson and J. Ban, (1992), BioTechniques. 13:572–575.) and proteins (Krajewski, S., J. M. Zapata and J. C. Reed, (1996), Anal. Biochem. 236:221–228) thus reducing detection sensitivity in the second and subsequent probing steps. A method which allows the detection and differentiation of more than one analyte in a test system would avoid the aforementioned drawbacks. The present invention describes a chemiluminescent detection method that provides a solution to this problem by achieving the sequential detection of two different target analytes on a single blot and eliminating the stripping and reprobing step.

A method is disclosed in a PCT application WO97/24460 for multiple chemiluminescent reporter gene assays. These assays are performed in solutions to detect the presence or quantity of two or more enzymes expressed by a reporter gene in a transfected cell. Use of a peroxidase enzyme is not disclosed as it is not a commonly used reporter enzyme in transfection experiments.

A method for using two or more enzymatically triggerable dioxetanes to simultaneously produce light of different wavelengths is disclosed in U.S. Pat. No. 4,931,223. Light emission is triggered from two or more different enzyme labels. Since all of the light emitting reactions are proceeding simultaneously, means for optically distinguishing the various signals is required, thus increasing complexity. A further disadvantage of this approach is the difficulty of finding multiple different fluorophores whose emission spectra do not overlap to some degree. When this occurs, signal from one label will be partially detected in the wavelength region of the signal from another label. Decreased measurement accuracy and precision result.

U.S. Pat. No. 5,656,207 describes dual chemiluminescent assays of two different analytes in a solution wherein the analytes or their binding partners are directly labeled with chemiluminescent compounds. The two signals are generated simultaneously and are distinguished kinetically or spectroscopically. Enzyme labels are not involved and no mechanism for stopping or controlling either reaction is disclosed.

U.S. Pat. No. 5,672,475 also discloses dual luminescent binding assays using two different chemiluminescent direct labels in a solution. The two chemiluminescent signals, one from a luminol derivative and the other from an acridinium ester compound, are generated separately by a change of pH process conditions. Enzyme labels are not involved. A step of treating the solution with nitric acid is involved which would render the method unusable for detecting analytes on a blotting membrane.

A radioactive method of sequential detection of blotted DNA and proteins has been reported in the literature. Signal distinguishable probes labeled with $^{32}P$, $^{35}S$, and digoxigenin have been used by simultaneous hybridizations and for differential or sequential autoradiography (Au L. C., K. J. Chang, C. M. Shih and G. W. Teh, BioTechniques. 16:680–683 (1994)). However, here the signal differentiation was based on the intensity of signal rather than on the qualitative signal differences as in the present methods.

A method for the sequential chemiluminescent detection of multiple antigens on western blots with the enhanced luminol HRP chemiluminescent substrate at each step has been reported (Krajewski, S., J. M. Zapata and J. C. Reed. Anal. Biochem. 236:221–228 (1996)). While this method is able to sequentially detect multiple analytes on a blot, it is more operationally complex than the present methods. The antigen-antibody-HRP complex in each detection step is detected by chemiluminescence and then rendered unreactive by reacting with a chromogenic substrate which deposits a colored product on the band. Although this method has the ability to sequentially detect multiple antigens, it is more cumbersome and labor intensive than the present methods since the blot needs to be reprobed with primary and secondary antibodies for each detection step. Moreover, each step requires the application of two detection reagents to report the presence of one analyte.

Several substances are known which inhibit or destroy peroxidase activity. Among these are hydrogen peroxide at high concentrations, imidazole, phenylhydrazine, (W. Straus, J. Histochem. Cytochem., 28(7), 645–652 (1980)) fluoride and cyanide ions (P. Tulkens, R. Wattiaux, Experientia, 24(3), 219–223 (1968)). A listing of several inhibitors appears in a publication by Pierce Chemical Co., Rockford, Ill. (1994–95 catalog pp. T-315, 316). U.S. Pat. No. 4,810,630 describes the use of a nonionic surfactant to inhibit endogenous peroxidase activity of whole blood in immunoassays using horseradish peroxidase conjugates with calorimetric detection.

SUMMARY OF THE INVENTION

It is an object of the present invention to provide a method for the sequential chemiluminescent detection of two analytes in a test system. It is another object of the present invention to provide a method in which the analytes are labeled with two different enzymes, more particularly when one of the enzymes is a peroxidase. It is another object of the present invention to provide a method in which two chemiluminescent detection reagents are sequentially contacted with the two enzyme-labeled analytes. It is a further object to provide a pair of detection reagents for use in such methods wherein the first detection reagent produces chemiluminescence by reacting with the peroxidase and the second reagent stops light production from the reaction of the peroxidase with the first reagent and initiates chemiluminescence from the second label enzyme. It is a further object to provide a method for the analysis of two analytes on a solid phase such as a blotting membrane. It is a further object to provide a method for the analysis of two analytes on a blotting membrane which eliminates the need to strip and reprobe blots. The methods of the present invention are suitable for the detection of multiple DNA markers or probes on a single Southern blot, for forensic DNA fingerprinting where more than multiple probes are used, multiplex DNA sequencing, for the detection of gene rearrangements, mutations and gene linkage, for the detection of multiple proteins in Western blots and other assays known in the art.

DESCRIPTION OF THE PREFERRED EMBODIMENTS

Definitions

Figure 1:
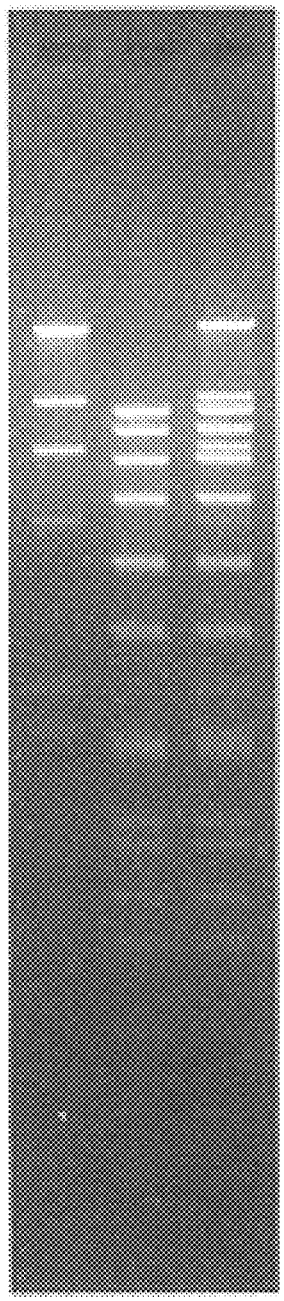
FIG. 1. Ethidium bromide stained agarose gel (1%) containing marker DNA. Lane 1: 300 ng biotinylated Hind III-digested lambda DNA; lane 2: 300 ng dig-labeled EcoRI-digested SPPI size marker DNA; lane 3: 100 ng biotinylated Hind III-digested lambda DNA and 300 ng dig-labeled EcoRI-digested SPPI size marker DNA.

Binding pair—two molecules or portions thereof which have a specific binding affinity for one another by virtue of multiple noncovalent attractions. Specific binding pairs are well known in the art and include by way of illustration antigen-antibody, hapten-antibody, antibody-antibody, complementary strands of DNA, DNA-RNA duplexes, DNA-complementary oligonucleotide, RNA-complementary oligonucleotide, DNA-anti-DNA antibody, DNA-DNA binding protein, biotin-avidin or streptavidin, receptor-ligand, protein A-IgG and lectin-carbohydrate.

Chemiluminescent peroxidase substrate—compounds which undergo an oxidation reaction in the presence of a peroxidase and a peroxide which results in the production of visible light. Several chemiluminescent peroxidase substrates are known in the art as described in (Kricka Ref). The most commonly used include the amino-substituted dihydrophthalazinediones such as luminol, isoluminol, N-alkyl and N,N-dialkylamino derivatives of luminol and isoluminol, 5-amino-6,7,8-trimethoxydihydrophthalazinedione and the benzo-fused homologs such as 7-dimethylamino-naphthalazinedione. Other chemiluminescent peroxidase substrates include the pyridazinoquinoxalinones as disclosed in U.S. Pat. No. 5,324,835. Still other chemiluminescent peroxidase substrates include the hydroxy-substituted dihydrophthalazinediones such as 5-hydroxy- and 6-hydroxyphthalazinediones and the hydroxynaphthalazine-dione as disclosed in commonly assigned U.S. Pat. No. 5,552,298, and a class of N-alkylacridan-9-carboxylate derivatives including esters, thioesters and sulfonimides as disclosed in commonly assigned U.S. Pat. No. 5,491,072 and U.S. Pat. No. 5,523,212 and U.S. Pat. No. 5,593,845.

Enhancer—a substance which promotes or prolongs the oxidative or peroxidative function of a peroxidase enzyme. The most effective enhancers are certain aromatic amines and phenols. Phenolic compounds known to enhance peroxidase reactions are described in G. Thorpe, L. Kricka, in

*Bioluminescence and Chemiluminescence, New Perspectives*, J. Scholmerich, et al, Eds., pp. 199–208 (1987), M. Ii, H. Yoshida, Y. Aramaki, H. Masuya, T. Hada, M. Terada, M. Hatanaka, Y. Ichimori, Biochem. Biophys. Res. Comm., 193(2), 540–5 (1993), and in U.S. Pat. Nos. 5,171,668 and 5,206,149 which are incorporated herein by reference. Preferred enhancers are selected from the group consisting of substituted phenols, unsubstituted and substituted naphthols, including but not limited to: p-phenylphenol, p-iodophenol, p-bromophenol, p-chlorophenol, 2,4-dichloro-phenol, p-imidazolylphenol, p-thiazolylphenol, p-hydroxy-acetanilide, p-hydroxycinnamic acid, (p-cyanomethylthio)-phenol and ring halogenated derivatives thereof, phenolindophenol, 2-naphthol, 6-bromo-2-naphthol 6-hydroxybenzothiazole, 2-cyano-6-hydroxybenzothiazole, firefly luciferin and dehydroluciferin.

Enzyme label—a functional enzyme associated with a member of a specific binding pair. The enzyme may be covalently linked to the specific binding partner, e.g. an enzyme-antibody conjugate or an enzyme-oligonucleotide conjugate. The enzyme may be indirectly linked or associated with the specific binding partner of the target by the use of an auxiliary specific binding partner to which the enzyme is covalently linked. An example of the latter relationship would be the use of a biotin-labeled oligonucleotide probe for a certain DNA sequence associated with an enzyme-avidin conjugate.

Genetic disease—pathologic condition caused by a genetic defect such as a mutation or a series of mutations. The mutation may be a point mutation, a single base substitution, a deletion, an insertion, a duplication or a transposition of bases or a combination of the above. Depending on the site or position and type of mutation, the mutant gene may or may not be expressed, if expressed, it may lead to the production of truncated or non-functional protein products or proteins with an altered amino acid sequence. Certain genetic mutations are recessive whereby both mutant alleles or copies of the gene on the homologous chromosomes must be present for disease symptoms to occur. Other genetic mutations are dominant whereby only one copy of the gene needs to bear the mutation for disease symptoms to occur. Individuals with one copy of the recessive mutant gene are carriers without any disease but can still transmit a copy of the mutant gene to offspring.

Heteroalkyl—a branched chain, straight chain or cycloalkyl group in which at least one non-terminal carbon atom is replaced by a non-carbon heteroatom such as B, N, O, S, P, Si, Se or Te. The heteroatom must be at least divalent.

Hydrolytic enzyme—are enzymes which catalyze the hydrolytic cleavage of various groups. Representative members include;

- esterases such as carboxyl esterase, acetylcholinesterase, butyrylcholinesterase and cholinesterase,
- glycosidases, such as galactosidase, glucosidase, glucuronidase, lactase, and N-acetylglucosaminidase,
- lipase, phospholipase,
- plant or animal phosphatases, including acid and alkaline phosphatases,
- protease enzymes such as chymotrypsin, trypsin, papain and pepsin and
- sulfatase enzymes.

Peroxidase enzyme—enzymes belonging to class EC 1.11.1.7 including horseradish peroxidase, cytochrome C peroxidase, glutathione peroxidase, microperoxidase, myeloperoxidase, lactoperoxidase, *Arthromyces ramosus* peroxidase (ARP) and soybean peroxidase.

Peroxide—compounds which act as a source of hydrogen peroxide which function as the primary substrate of the peroxidase. Exemplary peroxides include hydrogen peroxide, urea peroxide and perborate salts, especially sodium perborate.

Sample—materials upon which the methods of the present invention are performed to detect an analyte and includes human and animal bodily fluids, such as blood, serum, urine, saliva, sputum, CSF, seminal fluid and cell lysate, as well as food samples, water samples, plant samples, microbiological specimens and forensic specimens. Other types of samples as would occur to one of ordinary skill in the art are considered to be within the scope of the invention.

Solid support—test medium on which assay methods of the present invention can be carried out. Such supports include test strips, blotting membranes, filters, glass or plastic surfaces such as microscope slides and cover slips, microwells, test tubes, beads and the like as are known in the art of assays. The supports must be capable of capturing or immobilizing the target species-specific binding agent pair by physical adsorption or covalent linkage or both.

Target species—molecule or portion thereof whose presence is being probed. Target species must be capable of binding with a substance with which there is a specific binding affinity. In one embodiment, the target species will be bound to two different specific binding partners, each of which has a specific binding affinity. Exemplary target species include, nucleic acids such as ssDNA, dsDNA, RNA, oligonucleotides, proteins, peptides, antibodies, antigens, haptens, cell surface receptors, ligands, hormones, viruses, bacteria and the like.

Test system—comprises a solid support onto which are immobilized the analytes or target species to be detected. The test system also at different points during an analysis or assay will contain specific binding agents for the target species and label enzymes as a result of conducting the assay procedure.

The present invention concerns chemiluminescent methods for the sequential detection of two or more analytes in a test system using two or more enzyme-labeled binding partners and at least two reagents each comprising a chemiluminescent substrate for one of the enzymes. In particular, the choice of pair of enzymes and reagents is designed such that the chemiluminescence emitted by reaction of the first enzyme and first substrate can be rapidly stopped with a stop reagent, such as an enzyme inhibitor, and chemiluminescence produced by the second enzyme upon addition of the second enzyme substrate to the test system. In a preferred mode of practicing the invention the stop reagent is incorporated into a composition with the second enzyme substrate. The present methods are advantageously applied to detection of two or more analytes in a test system, for example on a blotting membrane, since the two detection reactions can be performed without any intervening steps or removal of enzymes, conjugates or analytes. Other operational advantages will be described further below.

More particularly, the invention concerns a method for sequentially detecting a first and second target species in a sample suspected of containing the two target species by two sequential chemiluminescent reactions comprising:

immobilizing the first and second target species on a solid support;

contacting the immobilized first and second target species with a first specific binding partner for the first target species and a second specific binding partner for the second target species to thereby form a first binding pair and a second binding pair;

providing a peroxidase enzyme as a label for the first binding partner and providing a second enzyme as a label for the second binding partner;

reacting the first binding pair with a chemiluminescent peroxidase substrate and a peroxide compound to produce a first chemiluminescent signal;

detecting the first target species by detecting the first chemiluminescent signal;

reacting the peroxidase with a peroxidase inhibitor to stop the first chemiluminescent signal;

reacting the second binding pair with a chemiluminescent substrate for the second enzyme to produce a second chemiluminescent signal; and detecting the second target species by detecting the second chemiluminescent signal.

Further the invention concerns a method for sequentially detecting a first and second target species in a sample suspected of containing the two target species by two sequential chemiluminescent reactions comprising:

immobilizing the first and second target species on a solid support;

contacting the immobilized first and second target species with a first specific binding partner for the first target species and a second specific binding partner for the second target species to thereby form a first binding pair and a second binding pair;

providing a peroxidase enzyme as a label for the first binding partner and providing a second enzyme as a label for the second binding partner;

reacting the first binding pair with a chemiluminescent peroxidase substrate and a peroxide compound to produce a first chemiluminescent signal;

detecting the first target species by detecting the first chemiluminescent signal;

reacting the second binding pair with a composition comprising a chemiluminescent substrate for the second enzyme and an inhibitor of the peroxidase enzyme to stop the first chemiluminescent signal and produce a second chemiluminescent signal; and detecting the second target species by detecting the second chemiluminescent signal.

The effectiveness of the present methods rests on satisfying several requirements for the enzyme/reagent pairs. The chemiluminescent reaction of the peroxidase with peroxide and the chemiluminescent compound must be capable of being rapidly stopped. This is best accomplished by both inhibiting the enzyme and converting unreacted substrate to a non-luminescent form, although performing only one of the two should also be effective.

The second reagent/enzyme pair must not only be robust enough to survive the conditions chosen to inhibit the peroxidase and destroy the peroxidase substrate, but also itself produce chemiluminescence efficiently. The reagents and conditions to stop the first enzymatic light-producing reaction must also not interfere with the integrity of the test system. The reagents and conditions must not displace, denature or otherwise alter biological analytes immobilized on the solid support used in the assay. The physical characteristics of the support must also not be adversely affected.

The choice of peroxidase enzymes as the first enzyme is based on the ready availability of conjugates and ease of conjugate preparation, availability of substrates, rapid catalytic turnover and the ability to inhibit peroxidase activity. The preferred peroxidase enzyme is horseradish peroxidase.

The substrate for the peroxidase enzyme can be any compound which, in combination with a peroxide, produces chemiluminescence when reacted with the peroxidase. Examples of chemiluminescent peroxidase substrates include diacylhydrazides including amino-substituted aromatic diacylhydrazides such as luminol and polycyclic aromatic diacylhydrazides as summarized in L.J Kricka and G. H. G. Thorpe, in Luminescence Immunoassay and Molecular Applications, K. Van Dyke and R. Van Dyke, eds., CRC Press, Boca Raton, 1990, pp. 77–98, hydroxy-substituted aromatic diacylhydrazides disclosed in U.S. Pat. No. 5,552,298, heterocyclic analogs of luminol such as (8-amino-5-chloro-7-phenylpyrido[3,4-d-pyridazine-1,4(2H,3H)dione (M. Ii, et al., Biochem. Biophys. Res. Comm., 193(2), 540–5 (1993)), pyridazinoquinoxalinones (U.S. Pat. No. 5,324,835), 1,3-disubstituted pyrazolo[4',3':5',6']pyrido-[2,3-d]-pyrazinediones (Y. Tominaga, et al., Tetrahedron Lett., 36, 8641-4 (1995)) and acridan compounds as disclosed in U.S. Pat. No. 5,491,072, U.S. Pat. No. 5,523,212 and U.S. Pat. No. 5,593,845, and 5,670,644 and PCT application WO98/02421. In a preferred embodiment, the peroxidase substrate is an acridan compound, more particularly an acridan selected from N-alkylacridan-9-carboxylate derivatives having the general formula:

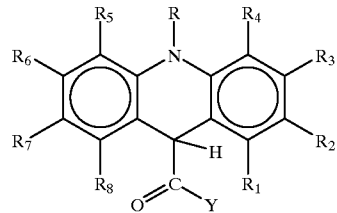

wherein R is selected from alkyl, heteroalkyl and aralkyl groups, wherein $R_1$ to $R_8$ are selected independently from groups which allow the production of light and adjacent pairs of groups $R_1$ to $R_8$ can be joined together to form a fused aromatic ring and wherein the group C(=O)Y is an ester, thioester or sulfonamide group.

It is desirable that the peroxidase substrate be capable of being rapidly and completely converted into a non-luminescent compound by a simple chemical process in order to stop the emission of chemiluminescence. The acridancarboxylate derivatives are particularly useful since they can be hydrolyzed to the corresponding carboxylic acid or salt which is incapable of producing chemiluminescence. Reaction with alkaline hydrogen peroxide ($^-$OOH) can also convert the acridancarboxylate derivatives to the corresponding non-luminescent percarboxylate compounds.

The second enzyme is preferably a hydrolytic enzyme, preferably selected from alkaline phosphatase, β-galactosidase and glucuronidase, more preferably alkaline phosphatase. Properties of alkaline phosphatase which are desirable for the present methods include the ready availability of conjugates and ease of conjugate preparation, availability of substrates, rapid catalytic turnover and robustness toward a variety of environmental conditions. It has been determined in the present work, for example, that enzymatic activity is not adversely affected even in the presence of relatively high concentrations of alkaline hydrogen peroxide at pH 10.

The substrate for the second enzyme is preferably an enzymatically triggerable dioxetane. Preferred dioxetanes have the formula:

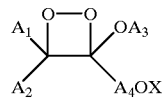

wherein $A_1$ and $A_2$ are groups which impart stability to the dioxetane, $A_3$ is selected from straight chain, branched chain or cycloalkyl, substituted alkyl, aryl and substituted aryl groups, $A_4$ is an aromatic ring group, preferably a substituted or unsubstituted phenyl or naphthyl group, OX is a substituent on the aromatic ring which triggers the production of chemiluminescence by reaction with an enzyme to cleave the O—X bond to produce an oxyanion and wherein the OX substituent occupies a position which is out of conjugation with the dioxetane ring. Any pair of groups selected $A_1$, $A_2$, $A_3$ and $A_4$ can be linked together to form a ring fused to the dioxetane ring. Suitable dioxetanes of this type are well known in the art and include as examples dioxetanes disclosed in U.S. Pat. Nos. 4,857,652, 4,952,707, 5,068,339, 5,112,960, 5,132,204, 5,220,005, 5,248,618, 5,578,253, 5,607,625, 5,631,167, 5,652,345 and 5,679,803, 5,707,559 and PCT application WO96/15122, the disclosures of which are incorporated herein by reference. In preferred enzymatically triggerable dioxetanes, $A_1$ and $A_2$ are each branched chain alkyl or cycloalkyl groups containing 3 to 8 carbon atoms or are joined together as a substituted or unsubstituted polycycloalkyl group having 6 to 10 carbon atoms, $A_3$ is an substituted or unsubstituted alkyl group having 1 to 10 carbon atoms, $A_4$ is a substituted or unsubstituted phenyl group and X is selected from a $PO_3^{2-}$ group, a galactoside group or a glucuronide group with the $PO_3^{2-}$ group being the most preferred. When $A_1$ and $A_2$ are joined together as the polycycloalkyl group such as an adamantyl, bicyclooctyl or bicyclononyl group with adamantyl being preferred, it can be unsubstituted or substituted with a group selected from halogens, particularly chlorine, lower alkyl, alkoxyl, phenyl or carboxyl groups. The group $A_3$ can also contain one or more substituents in place of the hydrogen atoms present. Representative groups include e.g. halogens, particularly fluorine and chlorine and water solubilizing groups such as carboxylate, sulfonate, sulfate or quaternary ammonium groups. The group $A_4$ can also contain one or more substituents in place of the hydrogen atoms on the ring, preferably a chlorine atom or alkoxy group.

The peroxidase reagent is generally used in aqueous buffer solution with the peroxide source and can contain additives such as surfactants and phenolic or other art-known peroxidase enhancers which contribute to the optimal performance of the chemiluminescent reaction, organic co-solvents and chelating agents to prevent interference by adventitious metal impurities. Preferred sources of peroxide are hydrogen peroxide, urea peroxide and perborate salts. Descriptions of preferred formulations and their components can be found in Applicant's U.S. Pat. Nos. 5,491,072, 5,523,212 and 5,593,845 which are incorporated herein by reference.

The dioxetane reagent for the chemiluminescent detection of the hydrolytic enzyme can be any of a number of stable enzymatically triggerable dioxetanes known in the art. The skilled artisan will readily be able to select an appropriate dioxetane from among the many disclosed in the art as illustrated by numerous patents cited above. The dioxetane must contain a group which can be removed by the particular enzyme being employed. When the enzyme is alkaline phosphatase, a preferred dioxetane is Lumigen PPD which has the structure shown below.

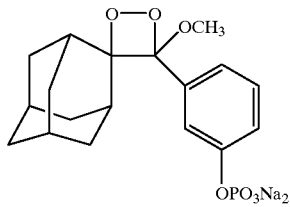

When the enzyme is β-galactosidase and glucuronidase, the dioxetane will contain, in place of the phosphate group, a galactoside or glucuronide group attached through an oxygen atom to the aromatic ring substituent of the dioxetane.

The detection reagent for the second enzyme comprises the substrate for the second enzyme in an aqueous buffer solution and, optionally, a peroxidase inhibitor. When the peroxidase inhibitor is not used, the composition of the reagent will be such that the application of this reagent to the test system destroys or renders non-luminescent the peroxidase substrate instead. It is preferred that the detection reagent for the second enzyme achieve both peroxidase inhibition and conversion of the peroxidase substrate to a non-luminescent form. A preferred detection reagent is prepared by adding one or more peroxidase inhibitors to a reagent containing a phosphate-substituted dioxetane. The detection reagent can also contain a surfactant enhancer, which improves the signal/background ratio of the enzymatically produced chemiluminescence. Suitable surfactant enhancers are known in the art and include polymeric onium salts, including quaternary phosphonium salts and ammonium salts, monomeric quaternary phosphonium and ammonium salts such as cetyltrimethylammonium bromide and dicationic surfactants, such as those described in Applicant's U.S. Pat. No. 5,451,347, the disclosure of which is incorporated herein by reference. Suitable polymeric quaternary phosphonium salts are described in Applicant's U.S. Pat. No. 5,393,469, the disclosure of which is incorporated herein by reference. Suitable polymeric quaternary ammonium salts are described in U.S. Pat. Nos. 5,145,772 and 5,547,836 the disclosures of which are incorporated herein by reference. A preferred detection reagent comprises: (1) the commercial reagent LUMI-PHOS PLUS (Lumigen, Southfield, Minn.) which contains the dioxetane LUMIGEN PPD in an alkaline buffer solution and a diphosphonium salt surfactant enhancer and (2) an appropriate reagent to stop the peroxidase-catalyzed chemiluminescence.

Peroxidase inhibitors useful in the practice of the present invention include those compounds known in the art and identified above which are known to inhibit the activity of peroxidase enzymes, and in particular horseradish peroxidase. This includes, without limitation, hydrogen peroxide alone or in combination with azide ion, cyanide ion, fluoride ion, imidazole, phenylhydrazine and periodate. Most preferred is hydrogen peroxide. It is a preferred embodiment, therefore, that the detection reagent for the second enzyme comprise LUMI-PHOS PLUS further containing hydrogen peroxide.

In another aspect, the invention concerns a method for sequentially detecting a first and second target species in a sample suspected of containing the two target species by two sequential chemiluminescent reactions comprising:

immobilizing the first and second target species on a solid support;

contacting the immobilized first and second target species with a first specific binding partner for the first target species and a second specific binding partner for the second target species to thereby form a first binding pair and a second binding pair;

providing a peroxidase enzyme as a label for the first binding partner and providing alkaline phosphatase as a label for the second binding partner;

reacting the first binding pair with an acridan-carboxylic acid derivative and a peroxide compound to produce a first chemiluminescent signal;

detecting the first target species by detecting the first chemiluminescent signal;

reacting the peroxidase with a peroxidase inhibitor to stop the first chemiluminescent signal;

reacting the second binding pair with a phosphate-substituted dioxetane to produce a second chemiluminescent signal; and detecting the second target species by detecting the second chemiluminescent signal.

In a further aspect, the invention concerns a method for sequentially detecting first and second target species comprising:

immobilizing the first and second target species on a solid support;

contacting the immobilized target species with a first specific binding partner for the first target species and a second specific binding partner for the second target species to thereby form a first binding pair and a second binding pair;

providing a peroxidase enzyme as a label for the first binding partner and providing alkaline phosphatase as a label for the second binding partner;

reacting the first binding pair with an acridancarboxylic acid derivative and a peroxide compound to produce a first chemiluminescent signal;

detecting the first target species by detecting the first chemiluminescent signal;

reacting the second binding pair with a composition comprising a phosphate-substituted dioxetane and an inhibitor of the peroxidase enzyme to stop the first chemiluminescent signal and produce a second chemiluminescent signal; and detecting the second target species by detecting the second chemiluminescent signal.

The present methods necessitate the design of a pair of enzyme detection reagents which allow the detection and quantitation of their corresponding enzymes rapidly, sensitively and specifically with no signal arising from the other enzyme. A particularly effective first enzyme-substrate pair are HRP and LUMIGEN PS-3. The rapid and highly sensitive chemiluminescent detection of HRP conjugates in blotting applications using this reagent is described in Akhavan-Tafti, H., R. DeSilva, Z. Arghavani, K. Sugioka, Y. Sugioka, and A. P. Schaap. 1994. p. 313–316. In A. Campbell, L. Kricka, P. Stanley (Eds.), Bioluminescence and Chemiluminescence Fundamentals and Applied Aspects, J. Wiley and Sons, Chichester. We have discovered that the reaction of HRP with LUMIGEN PS-3 can be rapidly switched off through a five-fold effect by contacting the glowing blot with a high pH buffer containing a high concentration of peroxide. The alkaline buffer (pH≧9.5) significantly diminishes peroxidase activity, while high concentrations of peroxide convert HRP into a catalytically inactive form, HRP compound III (Lundin, A. and L. Hallander. 1987. pp. 555–558. In Bioluminescence and Chemiluminescence New Perspectives, J. Scholmerich, R. Andreesen, A. Kapp, M. Ernst and W. G. Woods (Eds.), J. Wiley and Sons, Chichester). Further, the high pH buffer can hydrolyze the ester group of the HRP substrate, 2,3,6-trifluorophenyl 10-methylacridine-9-carboxylate to a non-luminescent carboxylate salt.

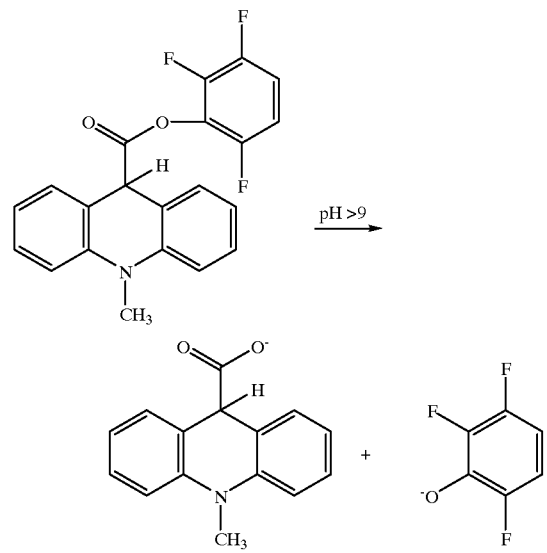

Alkaline hydrogen peroxide can also convert the ester group of the HRP substrate to a percarboxylate anion which would be incapable of generating chemiluminescence under the reaction conditions.

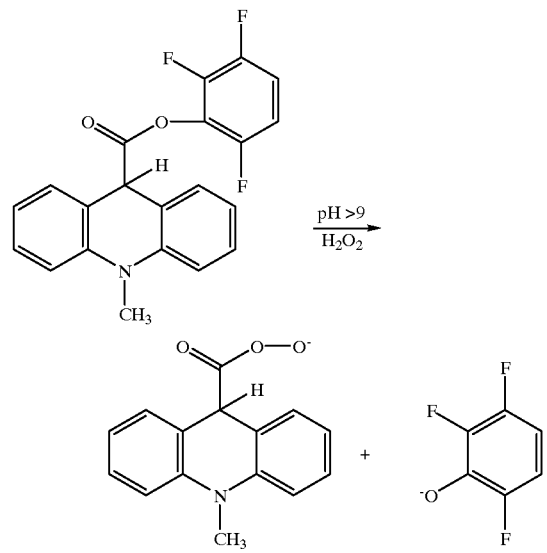

Contacting the HRP substrate with a strongly alkaline solution also accelerates its chemiluminescent autoxidation of by addition of $O_2$ to the small quantity of carbanion formed at the ring 9-position (F. McCapra, Accts. Chem. Res., 9(6), 201–8 (1976)). The combination of these five effects makes possible the rapid and complete extinction of light emission.

An especially effective second enzyme-substrate combination is alkaline phosphatase with LUMI-PHOS PLUS (Lumigen, Inc.). The latter reagent has proven to be a robust reagent for use in ultrasensitive blotting applications (Budowle, B., F. S. Baechtel, C. T. Comey, A. M. Giusti and L. Klevan, Electrophoresis, 16, 1559–1567 (1995)). Modification of LUMI-PHOS PLUS by addition of $H_2O_2$ provided a stable reagent which retained its utility for the chemiluminescent detection of alkaline phosphatase. Inclusion of up to at least 0.15% (v/v) of peroxide in Lumi-Phos Plus had no adverse affect on its performance in generating chemiluminescence or in destroying alkaline phosphatase activity. Importantly, the added peroxide and relatively high pH of this reagent permitted its use in stopping the aforementioned first chemiluminescent reaction.

In an additional embodiment of the present methods, a brief intermediate wash step with an alkaline buffer (pH>9, preferably ≧9.5) can be employed after detection of the bound peroxidase label but prior to wetting the solid support with the phosphatase detection reagent. The intermediate wash buffer can optionally contain the peroxidase inhibitor. The protocol can be simplified and the extra operation avoided by simply extending the time of incubation of the membrane in the second detection reagent to ≧15 min since the phosphatase detection reagent LUMI-PHOS PLUS is formulated at a high pH (9.6) to cause hydrolysis of the peroxidase substrate. It may also be advantageous for the composition containing the chemiluminescent substrate for the second enzyme to have a higher pH, e.g. ca. 10, in order to further diminish the time required to stop the peroxidase-catalyzed chemiluminescence.

In most types of applications based on a blotting technique, there is a need to obtain the maximum information with the minimum amount of sample, time and effort. Although stripping and reprobing achieve that end to some extent, they are tedious and because of the loss of membrane bound template DNA during stripping, the signal may be reduced and be counterproductive. It is estimated that up to 20 ng of membrane bound target DNA is lost during each stripping step depending on the method of probe removal. The loss of material and the time and expense of stripping and reprobing are reduced by the present methods in which the blots are simultaneously hybridized with two differentially labeled probes and detected sequentially with two different enzyme substrates. The present method is therefore advantageous for the sequential chemiluminescent detection method of two differentially labeled DNA size markers on a single blot. For example, the present methods can be applied to sequentially detect on a single Southern blot the CFTR genotypes harboring the $\Delta F_{508}$ mutation.

An assay for detecting two nucleic acid analytes performed according to the methods of the present invention comprises simultaneously hybridizing two differentially labeled probes, binding the two labels with their corresponding ligands or antibodies, one conjugated with a peroxidase and the other with a second, different enzyme and sequentially detecting the two label enzymes by sequential application of two chemiluminescent substrates. The first reagent contains a peroxidase substrate which signals the presence of the peroxidase-labeled bands. The second reagent contains a substrate for signaling the presence of the bands labeled with the second enzyme and further contains components which prevent continued light emission from the peroxidase-catalyzed reaction. The aforementioned test to detect the CFTR genotypes harboring the $\Delta F_{508}$ mutation on a single Southern blot is performed using two differently labeled probes, one specifically binding the normal sequence while the other specifically binds the mutant sequence.

There are numerous other applications where the sequential detection of two different nucleic acid analytes on a single blot can be applied. These include RFLP analysis by Southern blotting as used in forensic applications, gene expression analyses by northern, western, southwestern blotting, in-situ hybridization and in DNA sequencing. Additional applications of sequential detection using Southern blotting include identification of subspecies of a genus by simultaneous probing with genus and species specific probes followed by sequential chemiluminescent detection of the two probes; determination of gene linkage on large DNA fragments resolved by pulsed field gradient electrophoresis (PFGE) by simultaneously hybridizing with two differently labeled gene probes followed by sequential chemiluminescent detection; detection of juxtaposed genes in chromosomal translocations in cancer by simultaneous probing of Southern blot with the two gene probes and their chemiluminescent detection in a sequential manner.

In gene expression studies using northern and western blotting, sequential chemiluminescent detection can be used for measuring the levels of mRNA and protein of a specific gene (first detection) and normalizing its expression with an unaffected house-keeping gene such as β-actin or α-tubulin (second detection). There are numerous reports in the literature where stripping and reprobing of the same northern blot with a second probe is done to determine the levels of mRNA following an incubation or a treatment with a compound. Stripping and reprobing is also practiced in Western blotting. This can be avoided by simultaneously incubating the blot with two different antibodies and detect their binding to the membrane bound protein in a sequential manner as done for the mutation detection.

The sequential detection can also be used in DNA sequencing by using a differently labeled primer (different hapten) for the enzymatic primer extension of each DNA template to be sequenced. After blotting the sequencing ladder onto a membrane, the blot can be treated with the corresponding anti-hapten HRP and AP conjugates followed by sequential treatment with the HRP and AP substrates for the bands to emit light. The advantage is that the primer extension of two different templates can be done in a single tube and the DNA sequence ladders of each template for the nucleotides A, C, G and T can be differentiated by sequential detection.

In an alternate embodiment, a DNA sequencing protocol of a template DNA can be performed in two lanes instead of four by pooling two pairs of base-specific sequencing reactions, each pair containing two distinguishably labeled primers. For example primer with label 1 is used for the A and T-indicating reactions and the same primer but with label 2 and is used for the G and C-indicating reactions. The A and G reaction products are pooled and electrophoresed in one lane; the T and C reaction products are pooled and electrophoresed in another lane. Application of the sequential detection method reveals the sequence of all four bases in only two lanes.

The present method for the detection of at least two analytes requires only the primary and secondary antibody binding steps; no stripping or reprobing is required. Hybrid techniques involving multiple HRP detection steps and a final AP detection step are contemplated as well. Application of the present sequential detection techniques to more than two analytes in a test system can be accomplished by stripping bound ligands and enzymes from the solid support and reprobing the test system with new specific ligands for a new round of sequential detection according to the present methods. A further extension of the present methods would involve the sequential chemiluminescent detection of three or four analytes by simultaneously probing with multiple differentially labeled probes (e.g. biotin, fluorescein, digoxigenin, dinitrophenol) and sequentially detecting the labeled probes using several different enzymes (e.g. HRP, AP, β-galactosidase and glucuronidase) by inhibiting the chemiluminescent signal generated in each preceding step.

EXAMPLES

Example 1
Chemiluminescent Substrates.

The chemiluminescent HRP detection reagent LUMIGEN PS-3 was obtained from Lumigen, Inc. The reagent is prepared by combining two solutions in a 1:40 ratio. The working solution contains the 2,3,6-trifluorophenyl 10-methyl-acridine-9-carboxylate, a peroxide, a phenol enhancer compound, and a nonionic surfactant in pH 8.0 buffer. EDTA, which is usually included in the reagent, was excluded.

Chemiluminescent AP detection reagents were prepared by adding various quantities of 30% $H_2O_2$ to LUMI-PHOS PLUS (Lumigen, Inc.). A concentration of 0.15% $H_2O_2$ was selected for the method development work. The working phosphatase detection reagent (PDR), was prepared by adding 0.5 mL of 30% $H_2O_2$ to 100 mL of LUMI-PHOS PLUS.

Example 2
Detection of DNA Markers

The sequential detection of DNA was first demonstrated using two differentially labeled DNA size markers, a biotinylated Hind III enzyme-digested lambda phage DNA (Life Technologies, Gaithersburg, Md.), and a digoxigenin-labeled EcoRI enzyme-digested SPPI marker DNA (Boehringer Mannheim, Indianapolis, Ind.). These size markers were fractionated individually in separate lanes and as a mixture in a third lane in 1% agarose gel containing ethidium bromide (FIG. 1). The gel was depurinated (0.25 M HCl), denatured (0.5 N NaOH, 1.5 M NaCl), neutralized (0.5 M Tris-HCl, pH 7.5, 1.5 M NaCl), and vacublotted onto a neutral Hybond N nylon membrane (Amersham, Arlington Heights, Ill.). The membrane was baked at 80° C. for 2 h.

Figure 2:
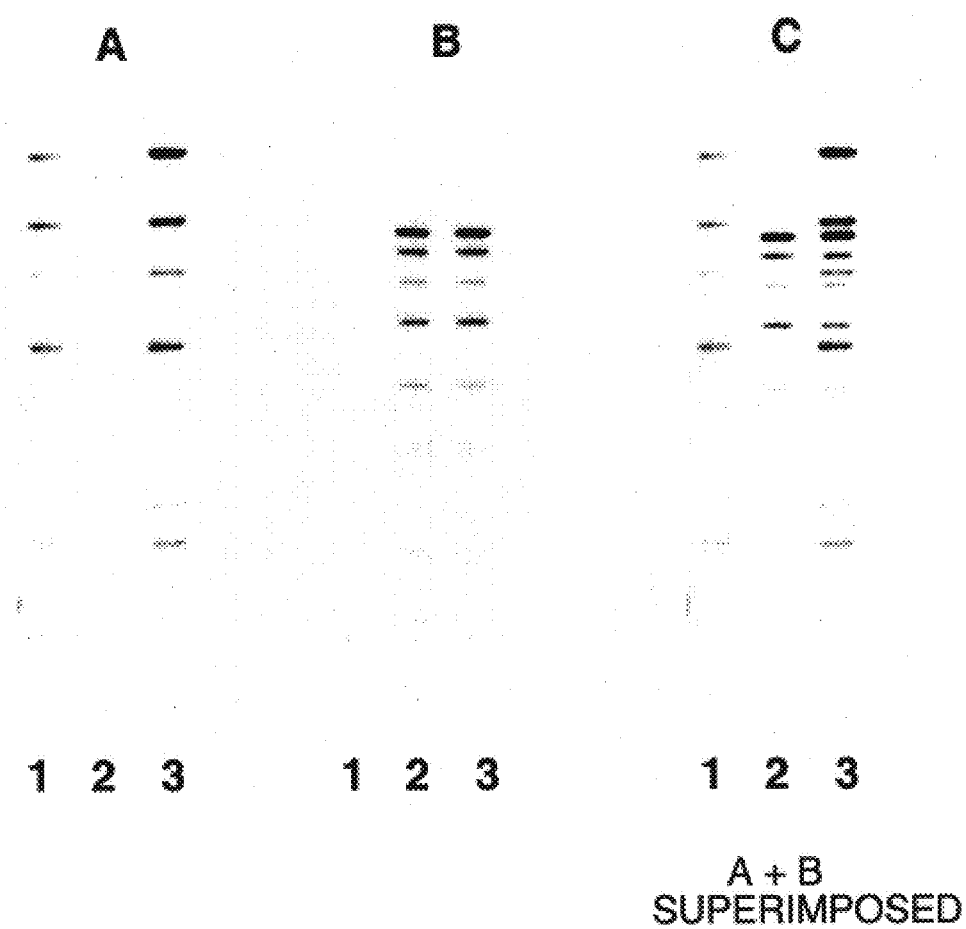
FIG. 2. Sequential detection of the blotted DNA size markers shown in FIG. 1. A: HRP substrate (LUMIGEN PS-3) detection of biotinylated HindIII digested lambda DNA; B: same blot further treated with AP substrate (PDR) for the detection of digoxigenin-labeled SPPI DNA marker; C: superimposed picture of the bands in (A) and (B) to show that the band patterns correspond to those of the ethidium stained gel of FIG. 1.
Figure 3:
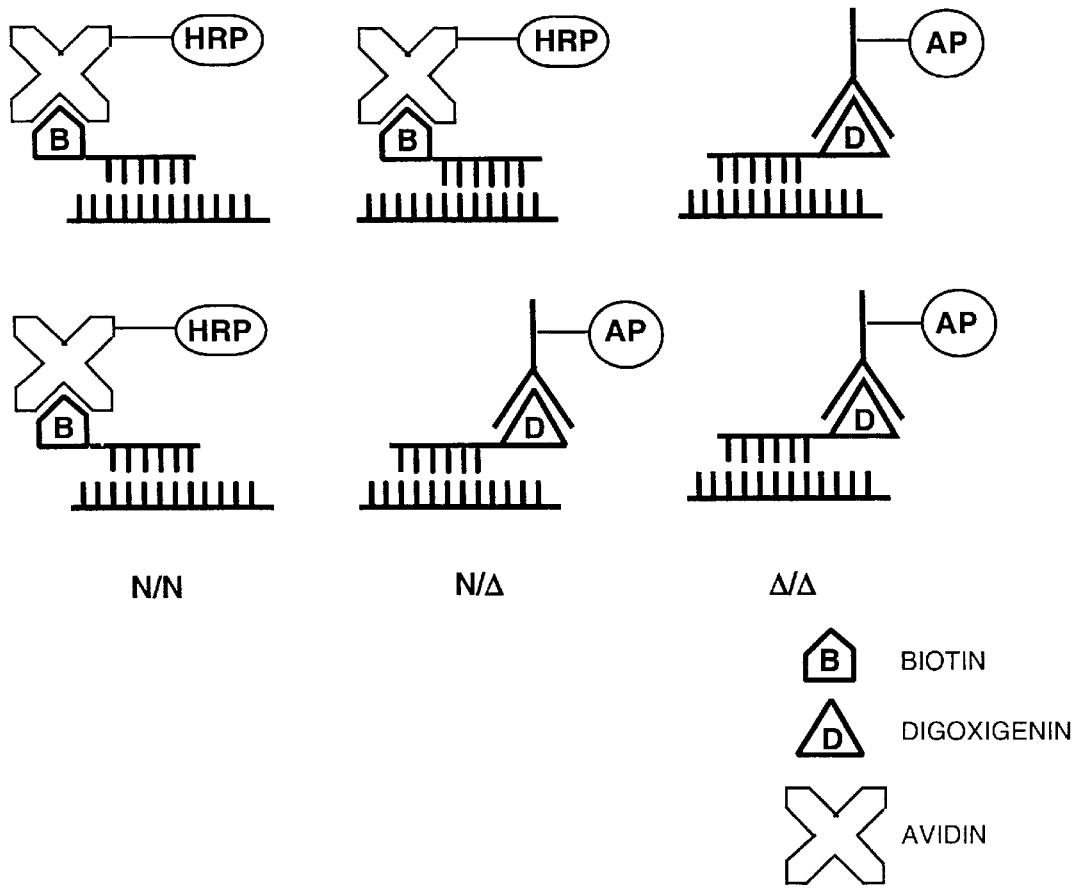
FIG. 3. Schematic diagram of the sequential detection of CFTR genotypes with HRP and AP substrates.
Figure 3:
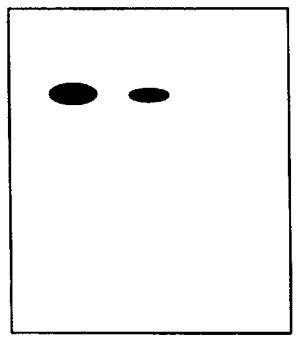
Figure 3:
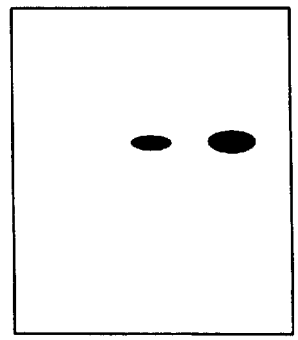

The blots were first washed for 15 minutes in 1× wash buffer (0.1 M maleic acid, 0.15 M NaCl, pH 7.5, 0.3% Tween 20) and blocked for 1 h in 2% blocking buffer (Blocking Reagent—Boehringer Mannheim, dissolved in 0.1 M maleic acid, 0.15 M NaCl, pH 7.5). The working concentrations of the enzyme conjugates were 1:5000 dilutions in 2% blocking buffer. The blots containing the DNA size markers were treated with avidin-HRP (Pierce, Rockford, Ill.) and anti-digoxigenin-AP (Boehringer Mannheim, Indianapolis, Ind.) enzyme conjugates followed by sequential treatments with the chemiluminescent substrates LUMIGEN PS-3 for HRP and PDR for AP. Both the enzyme and substrate treatments were performed at room temperature; the substrate incubations were done in the dark to reduce exposure of the substrate to light. Following the enzyme conjugate treatment, the blots were washed twice for 20 min each in 1× wash buffer and then reacted with the HRP substrate for 5 min. Excess substrate was removed by gently pressing the blots between a pair of transparent plastic sheets. The blots were exposed to X-ray film for a time period generally ranging from a few seconds to minutes to obtain optimal signal and background. FIG. 2A shows the resulting image obtained after application of the peroxidase substrate. Upon treatment with Lumigen PS-3 (see Ex. 1), chemiluminescence was generated only from the avidin-HRP bound biotinylated HindIII digested lambda DNA bands (lanes 1 and 3).

Next the blots were rinsed 5 min each in 1× wash buffer and in AP detection buffer (100 mM Tris HCl, pH 9.5, 100 mM NaCl, 50 mM $MgCl_2$) followed by another 5 min treatment with the PDR of Example 1. FIG. 2B shows the resulting image obtained after application of the PDR. The HRP-generated signal from lanes 1 and 3 ceases and AP-catalyzed chemiluminescence commenced from the digoxigenin-labeled SPPI-EcoRI size markers in lanes 2 and 3. Superposition of the lanes in FIGS. 2A and 2B (FIG. 2C) reveals all of the band sizes in lane 3 as confirmed by comparison to the pattern seen in the lanes of the ethidium bromide stained agarose gel shown in FIG. 1.

Example 3

Southern Blot Analysis of CFTR Genotypes

The sequential detection strategy described above was applied to detect and differentiate the genotypes of the CFTR gene with the $\Delta F_{508}$ mutation. The DNA of CFTR genotypes for the $\Delta F_{508}$ mutation (obtained from Coriell Cell Repositories, Camden, N.J.), wild type (N/N), heterozygous (N/$\Delta F_{508}$) and homozygous ($\Delta F_{508}$/$\Delta F_{508}$) were amplified by polymerase chain reaction (PCR) employing primers for the region of exon 10 containing the mutation (primers synthesized by Oligos etc., Wilsonville, Oreg.). The primers had the sequences: 5' ACTTCACTTCTAATGATGATTATG 3' (SEQ ID NO:1) and 5' CTCTTCTAGTTGGCAT-GCTTTGAT 3' (SEQ ID NO:2). The PCR products were electrophoresed on a 1% agarose gel and Southern blotted as described above for the DNA size markers. The blot was hybridized simultaneously with a pair of differentially labeled (biotin and digoxigenin) oligonucleotide probes, one complementary to the normal and the other to the mutant allele. The labeled oligonucleotides were 5' biotin—ATATCATCTTTGGTGTTTCCT 3' (SEQ ID NO:3) (normal) and 5' digoxigenin—GAAAATATCATTGGTGTTTCC 3' (SEQ ID NO:4) (mutant).

The conditions of prehybridization and hybridization of the blot were 52° C. for 1 h and overnight, respectively, using a buffer containing 6×SSC (0.9 M sodium chloride, 0.09 M sodium citrate, pH 7.0), 0.01 M EDTA, pH 8.0, 5× Denhardt's solution (0.1% Ficoll Type 400, 0.1% polyvinylpyrrolidone, 0.1% bovine serum albumin), 0.5% sodium dodecyl sulfate (SDS) and 100 μg/ml denatured salmon sperm DNA (Life Technologies). The post-hybridization washes were done at 52° C. for 20 min each in 2×SSC, 0.1% SDS and 0.5×SSC, 0.1% SDS. The blots containing the DNA hybridized with the CFTR allele specific oligonucleotides were treated as described above for the washing, blocking, binding of antibodies and detection.

Figure 4:
FIG. 4. Sequential detection of CFTR genotypes. Southern blotted PCR-amplified sequences of a region of exon 10 of the CFTR gene from each of the three genotypes, N/N, N/$\Delta F_{508}$ and $\Delta F_{508}/\Delta F_{508}$ were simultaneously hybridized with a pair of labeled oligonucleotides specific for the normal (biotin labeled) and/or mutant (digoxigenin labeled) alleles and then incubated with avidin-HRP and anti-digoxigenin-AP conjugates. A: Detection by HRP-generated chemiluminescence of the genotypes containing the normal allele; Lane 1: N/N, Lane 2: N/$\Delta$; B: Detection of the same blot by AP-generated chemiluminescence of the genotypes with the mutant $\Delta F_{508}$ allele; Lane 2: N/$\Delta$ and Lane 3: $\Delta/\Delta$.
Figure 4:

The amplified normal (24 bp) and mutant sequence products (27 bp) were sufficiently resolved to clearly discriminate the two products on the blots. Simultaneous incubation with avidin-HRP and anti-digoxigenin-AP conjugates and detection as described above achieved the selective detection first of the genotypes containing the normal allele (N/N and N/Δ) by HRP-generated chemiluminescence (FIG. 4A) and, in the second step, of those with the mutant $\Delta F_{508}$ allele N/Δ and Δ/Δ (FIG. 4B).

The foregoing description and examples are illustrative and not to be considered restrictive. It is recognized that modifications of the specific compounds and methods disclosed can be made without departing from the spirit and scope of the present invention. The scope of the invention is limited only by the appended claims.

We claim:

1. A method for sequentially detecting a first and second target species in a sample suspected of containing the first and second target species by two sequential chemiluminescent reactions comprising:

immobilizing the first and second target species on a solid support;

contacting the immobilized first and second target species with a first specific binding partner for the first target species and a second specific binding partner for the second target species to thereby form a first binding pair and a second binding pair;

providing a peroxidase enzyme as a label for the first binding partner and providing a second enzyme as a label for the second binding partner;

reacting the first binding pair with a chemiluminescent peroxidase substrate and a peroxide compound to produce a first chemiluminescent signal;

detecting the first target species by detecting the first chemiluminescent signal;

reacting the second binding pair with a composition comprising a chemiluminescent substrate for the second enzyme and an inhibitor of the peroxidase enzyme to stop the first chemiluminescent signal and produce a second chemiluminescent signal; and detecting the second target species by detecting the second chemiluminescent signal.

2. The method of claim 1 wherein the first specific binding partner is labeled with a first hapten, the second specific binding partner is labeled with a second hapten which is different from the first hapten, the peroxidase enzyme is provided as a conjugate with a third specific binding partner which binds the first hapten, and the second enzyme is provided as a conjugate with a fourth specific binding partner which binds the second hapten.

3. The method of claim 2 wherein the first and second haptens are independently selected from the group consisting of biotin, fluorescein and digoxigenin.

4. The method of claim 1 wherein the first specific binding partner is directly labeled with the peroxidase enzyme.

5. The method of claim 1 wherein the second specific binding partner is directly labeled with the second enzyme.

6. The method of claim 1 wherein the second enzyme is a hydrolytic enzyme.

7. The method of claim 6 wherein the hydrolytic enzyme is selected from alkaline phosphatase, β-galactosidase and glucuronidase.

8. The method of claim 6 wherein the hydrolytic enzyme is alkaline phosphatase.

9. The method of claim 1 wherein the peroxidase enzyme is horseradish peroxidase.

10. The method of claim 1 wherein the first and second target species comprise a first region of a nucleic acid and a second region of the nucleic acid and wherein the first specific binding partner is a first oligonucleotide probe complementary to the first region of the nucleic acid and the second specific binding partner is a second oligonucleotide probe complementary to the second region of the nucleic acid.

11. The method of claim 10 used for determining the presence of a genetic mutation.

12. The method of claim 11 wherein the first and second target species comprise a first nucleotide sequence of a normal gene and a second nucleotide sequence containing a mutation of the gene, wherein the first specific binding partner is an oligonucleotide probe complementary to the first nucleotide sequence and the second specific binding partner is an oligonucleotide probe complementary to the second nucleotide sequence.

13. The method of claim 1 used in a DNA sequence analysis.

14. The method of claim 1 wherein the first and second target species are first and second proteins and the method is used in a Western blot assay.

15. The method of claim 1 wherein the chemiluminescent substrate for the second enzyme is an enzymatically triggerable dioxetane.

16. The method of claim 15 wherein the dioxetane has the formula:

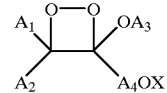

wherein $A_1$ and $A_2$ are groups which impart stability to the dioxetane, $A_3$ is selected from straight chain, branched chain or cycloalkyl, substituted alkyl, aryl and substituted aryl groups, $A_4$ is an aromatic ring group substituted with a triggerable OX substituent in a position which is out of conjugation with the dioxetane ring wherein reaction of the OX substituent with an enzyme to cleave the O—X bond triggers the production of chemiluminescence, and any pair of groups selected from $A_1$, $A_2$, $A_3$ and $A_4$ can be linked together to form a ring fused to the dioxetane ring.

17. The method of claim 16 wherein $A_1$ and $A_2$ are joined together as a substituted or unsubstituted polycycloalkyl group having 6 to 10 carbon atoms, $A_3$ is a substituted or unsubstituted alkyl group having 1 to 10 carbon atoms, $A_4$ is a substituted or unsubstituted phenyl group and X is selected from a $PO_3^{2-}$ group, a galactoside group or a glucuronide group.

18. The method of claim 17 wherein the group OX is a phosphate group.

19. The method of claim 18 wherein the dioxetane has the formula:

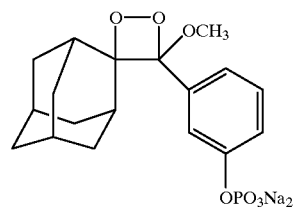

20. The method of claim 1 wherein the chemiluminescent peroxidase substrate is selected from N-alkylacridan-9-carboxylate derivatives having the general formula:

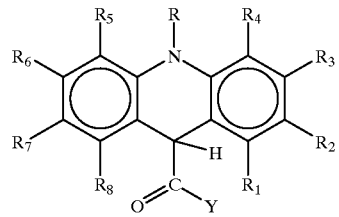

wherein R is selected from alkyl, heteroalkyl and aralkyl groups, wherein $R_1$ to $R_8$ are selected independently from groups which do not interfere with the production of light and wherein adjacent pairs of groups $R_1$ to $R_8$ can constitute the group CH=CH—CH=CH thereby forming a benzo-fused ring and wherein the C(=O)—Y group is an ester, thioester or sulfonamide group.

21. The method of claim 20 wherein the N-alkylacridan-9-carboxylate derivative has the formula:

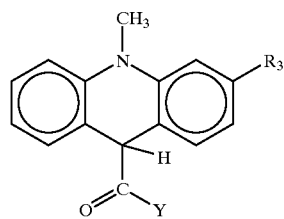

wherein R₃ is selected from H, Cl or a methoxy group.

22. The method of claim 21 wherein Y is a 2,3,6-trifluorophenoxy group.

23. The method of claim 22 wherein R₃ is the H atom.

24. The method of claim 1 wherein the solid support is selected from the group consisting of test strips, blotting membranes, filters, glass slides, plastic slides, microwells, test tubes and beads.

25. The method of claim 24 wherein the solid support is a blotting membrane.

26. The method of claim 1 wherein the peroxide is selected from the group consisting of hydrogen peroxide, urea peroxide and perborate salts.

27. The method of claim 1 wherein the chemiluminescent peroxidase substrate and the peroxide are provided in an aqueous reagent composition further comprising a phenol enhancer.

28. The method of claim 27 wherein the composition containing the peroxidase substrate further comprises a surfactant.

29. The method of claim 1 wherein the peroxidase inhibitor is selected from hydrogen peroxide alone or in combination with azide ion, cyanide ion, fluoride ion, imidazole, phenyihydrazine and periodate.

30. The method of claim 1 wherein the peroxidase inhibitor is hydrogen peroxide.

* * * * *